United States Patent [19]
Hutson

[11] Patent Number: 5,755,225
[45] Date of Patent: May 26, 1998

[54] MEDICAL TUBE-RETAINING DEVICE

[75] Inventor: Teresa H. Hutson, Savannah, Ga.

[73] Assignee: Hutson & Associates, Inc., Savannah, Ga.

[21] Appl. No.: 720,423

[22] Filed: Sep. 30, 1996

[51] Int. Cl.$^6$ .......................... A61M 16/00; A61M 5/00
[52] U.S. Cl. .......................... 128/207.18; 128/DIG. 26; 128/207.14; 128/200.26; 604/174; 604/178
[58] Field of Search .......................... 128/200.26, 207.14, 128/207.15, 207.17, 207.18, 207.13, DIG. 26; 604/174, 177, 178, 179, 180

[56] References Cited

U.S. PATENT DOCUMENTS

| | | | |
|---|---|---|---|
| 3,046,989 | 7/1962 | Hill | 128/207.13 |
| 3,834,380 | 9/1974 | Boyd | 128/133 |
| 3,990,454 | 11/1976 | Schlesinger | 128/349 |
| 3,993,081 | 11/1976 | Cussell | 128/207.18 |
| 4,742,824 | 5/1988 | Payton et al. | 128/207.18 |
| 4,823,789 | 4/1989 | Beisang | 128/207.18 |
| 4,932,943 | 6/1990 | Nowak | 604/178 |
| 5,069,206 | 12/1991 | Crosbie | 128/200.26 |
| 5,084,026 | 1/1992 | Shapiro | 604/174 |
| 5,117,818 | 6/1992 | Palfy | 128/207.18 |
| 5,156,641 | 10/1992 | White | 128/207.18 |
| 5,172,688 | 12/1992 | Dillon | 128/207.18 |
| 5,470,321 | 11/1995 | Forster et al. | 604/174 |

OTHER PUBLICATIONS

Attached description of commercial product with color photocopies; Product available prior to Sep. 30, 1996.

Primary Examiner—Vincent Millin
Assistant Examiner—William J. Deane, Jr.
Attorney, Agent, or Firm—Adams Law Firm, P.A.

[57] ABSTRACT

A tube-retaining device is provided for holding a medical tube in a fixed position on a patient's body proximate the tube insertion site. The tube-retaining device includes a base, and clamp mounted on the base for engaging and holding the tube. The clamp includes first and second spaced-apart arms pivotably attached for movement between an open tube-receiving position and a closed tube-enclosing position. Locking teeth are formed on the arms for adjusting the space between the arms in the closed position. The clamp is adjustable for accommodating different size tubes.

16 Claims, 4 Drawing Sheets

MEDICAL TUBE-RETAINING DEVICE

TECHNICAL FIELD AND BACKGROUND OF THE INVENTION

This invention relates to a medical tube-retaining device for holding a medical tube, such as a nasal endotracheal tube or IV catheter, in fixed position on the body near the tube insertion site. For nasal endotracheal tubes, the invention helps prevent displacement of the tube within the trachea to guard against unintentional extubation. The invention further prevents accidental disconnection of the anesthesia circuit. The invention can be quickly and securely anchored in several different places on the patient, such as the nose and forehead in the case of nasal endotracheal tubes, and on the forearm in the case of IV catheters.

According to one prior art technique of retaining a medical tube near the tube insertion site, one or more adhesive strips are applied directly over the tube and to the skin of the patient. In order to adjust the position of the tube, the adhesive strip must be removed from the skin and then reapplied in the desired location. This significantly weakens the holding strength of the adhesive, and often requires the placement of additional strips on the tube and skin to properly anchor the tube. Natural body secretions and slight inadvertent contact with the tube during surgery further reduce the ability of the strip to properly retain the tube.

Other prior art devices using a clamp attached to an adhesive strip are likewise ineffective. These such devices are generally applicable only for a single, specific tube size and do not effectively restrict sliding movement of the tube within the clamp. Moreover, insertion and removal of the tube into and out of the clamp is generally inconvenient.

SUMMARY OF THE INVENTION

Therefore, it is an object of the invention to provide a tube-retaining device which conveniently and securely retains the tube in a fixed position on the body near the tube insertion site.

It is another object of the invention to provide a tube-retaining device which includes a clamp that is easily opened and closed.

It is another object of the invention to provide a tube-retaining device which restricts sliding movement of the tube within the clamp.

It is another object of the invention to provide a tube-retaining device which includes a clamp that automatically closes when the tube is placed within the clamp.

It is another object of the invention to provide a tube-retaining device which includes a clamp that automatically ejects the tube when the clamp is opened.

It is another object of the invention to provide a tube-retaining device which includes a clamp that is readily adjustable to securely hold different size tubes.

These and other objects of the present invention are achieved in the preferred embodiments disclosed below by providing a tube-retaining device for holding a medical tube in a fixed position on a patient's body proximate the tube insertion site. The tube-retaining device includes a base, and a clamp mounted on the base for engaging and holding the tube. The clamp includes first and second spaced-apart arms pivotably attached for movement between an open tube-receiving position and a closed tube-enclosing position. Adjustment means are provided for adjusting the space between the arms in the closed position. The clamp is therefore adjustable for accommodating different size tubes.

According to one preferred embodiment of the invention, the base comprises a flexible patch with an adhesive coating on its back surface for adhering the tube-retaining device directly to the skin of the patient.

According to another preferred embodiment of the invention, a release paper backing removably covers the back surface of the patch.

According to yet another preferred embodiment of the invention, the arms of the clamp include a slip-resistant inner lining for frictionally engaging the tube.

According to yet another preferred embodiment of the invention, the slip-resistant inner lining is formed of rubber.

According to yet another preferred embodiment of the invention, the arms are pivotably connected together at respective proximal ends thereof. The clamp further includes a mounting member having first and second hinge joints connected to respective arms and providing pivoting movement of the arms between the open tube-receiving position and the closed tube-enclosing position.

According to yet another preferred embodiment of the invention, the adjustment means includes complementary locking teeth formed on each of the arms. The teeth have respective engaging surfaces to provide locking adjustment of the space occupied by the tube and defined by the arms in the closed position.

According to yet another preferred embodiment of the invention, first and second grip extensions are formed on one of the arms and on the mounting member, to facilitate locking adjustment of the space defined by the arms in the closed position.

BRIEF DESCRIPTION OF THE DRAWINGS

Some of the objects of the invention have been set forth above. Other objects and advantages of the invention will appear as the description proceeds when taken in conjunction with the following drawings, in which.

DESCRIPTION OF THE PREFERRED EMBODIMENT AND BEST MODE

Figure 1:
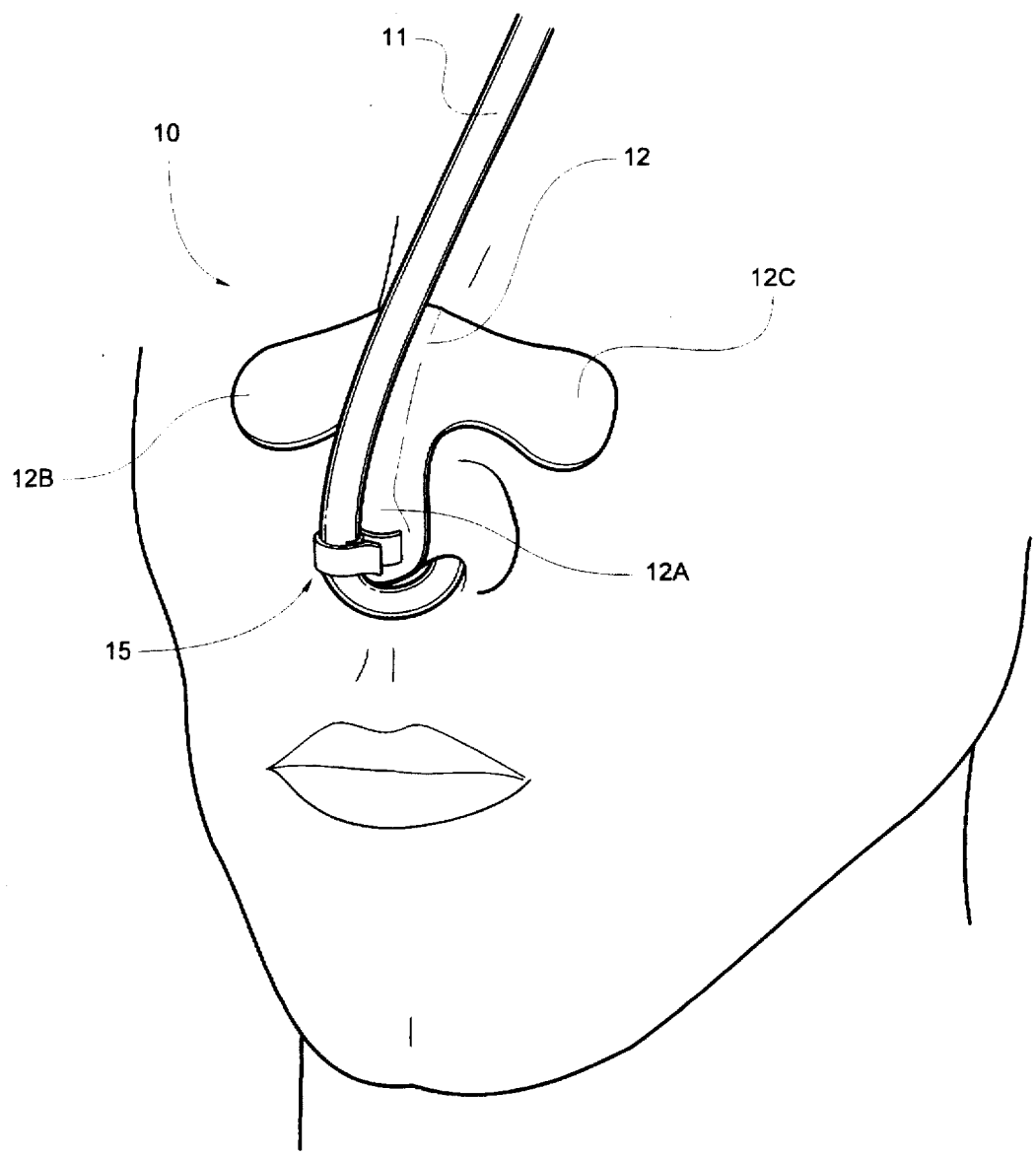
FIG. 1 is a perspective view of the tube-retaining device according to one preferred embodiment of the present invention, and showing the device secured to the nose of a patient for retaining a nasal endotracheal tube in a desired fixed position.

Referring now specifically to the drawings, a medical tube-retaining device according to the present invention is illustrated in FIG. 1 and shown generally at reference numeral 10. The tube-retaining device 10 is applicable for holding a medical tube 11, such as a nasal endotracheal tube or IV catheter, in a fixed position near the tube insertion site. For nasal endotracheal tubes, the device 10 helps maintain proper positioning of the tube 11 within the trachea and nostril to avoid injuring soft tissue inside the nose, and to avoid unintentional extubation. The device 10 further prevents accidental disconnection of the anesthesia circuit.

Figure 2:
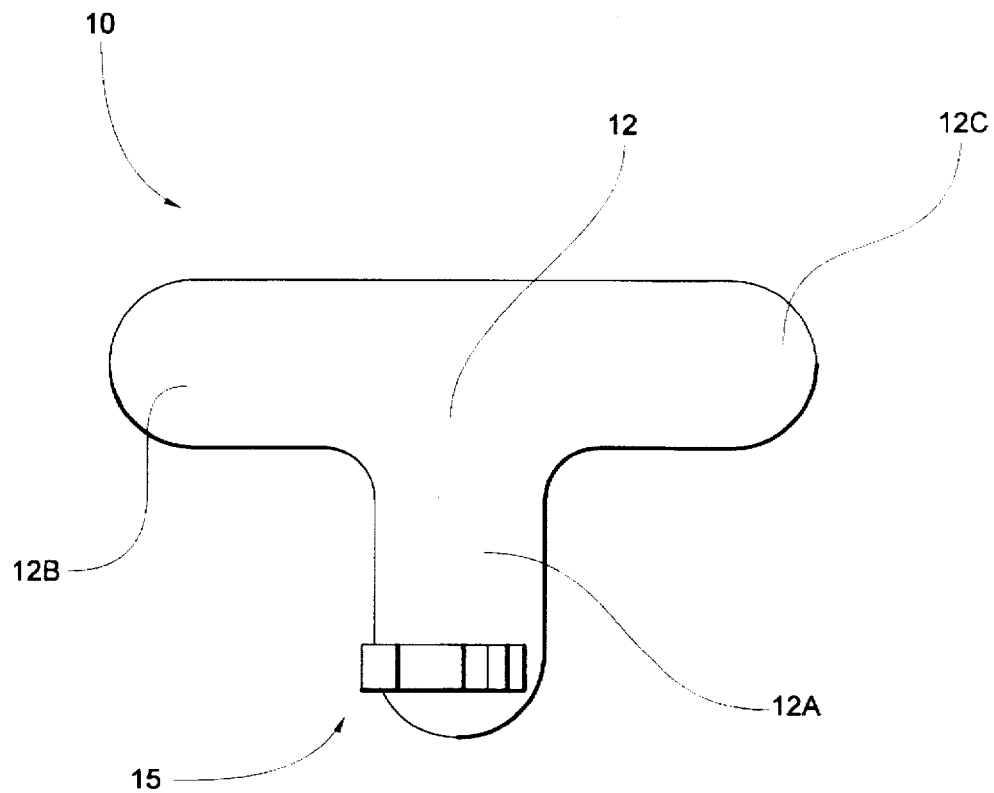
FIG. 2 is a side elevational view of the tube-retaining device shown in FIG. 1 with the clamp in the open position.

Referring to FIGS. 1 and 2, the device 10 includes a patch 12 formed of thin flexible plastic or paper and having an adhesive coating on its back surface for adhering the device 10 directly to the skin of the patient. The adhesive surface is covered with a release paper which is peeled away to expose the adhesive before positioning the patch 12 on the nose, as shown in FIG. 1. According to one embodiment, the patch 12 has a front tab 12A which extends over the front of the nose and side tabs 12B and 12C extending outwardly on opposite sides of the nose.

A clamp 15 is attached to the front tab 12A for holding the tube 11 as it exits the nostril and extends upwardly over the nose of the patient. The clamp 15 is integrally formed of a molded plastic material, and includes a mounting member 16 attached to the patch 12 and a pair of arcuate, slightly resilient arms 17 and 18. The arms 17 and 18 are pivotably connected together at a center connecting point 21, and are connected to the mounting member 16 at first and second hinged joints 22 and 23, respectively. The arms 17 and 18 are movable between an open tube-receiving position, shown in FIG. 3, and one of two closed positions, shown in FIGS. 4 and 5.

Figure 4:
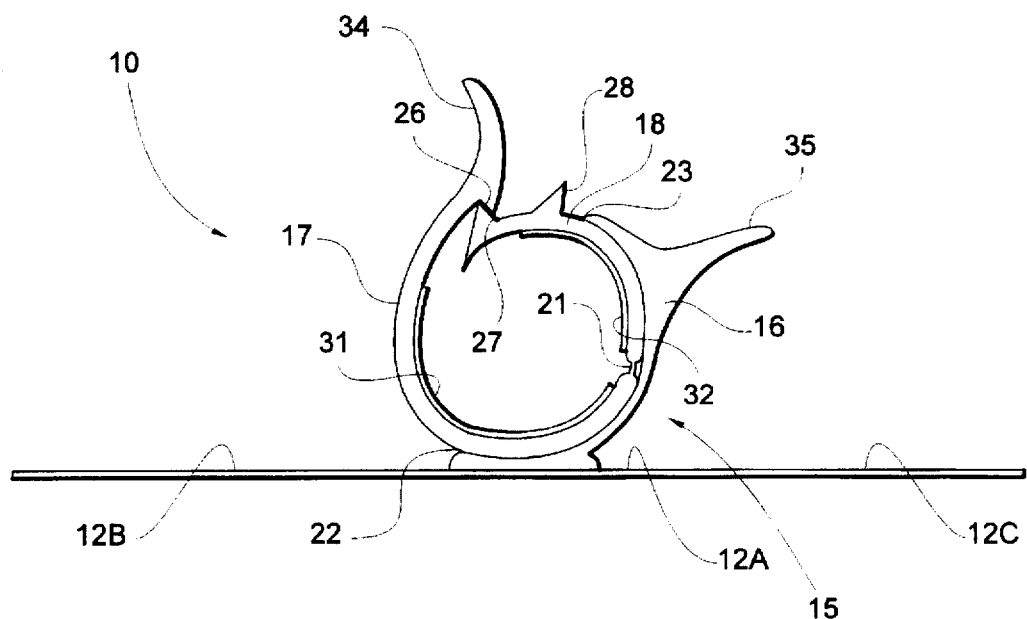
FIG. 4 is a side elevational view of the tube-retaining device with the clamp in a first closed position.
Figure 5:
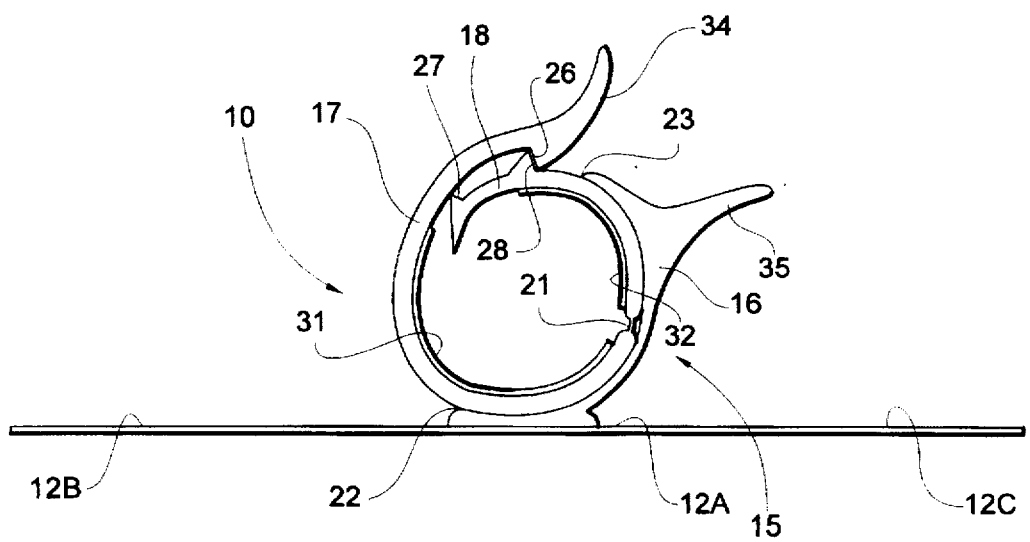
FIG. 5 is a side elevational view of the tube-retaining device with the clamp in a second closed position.

Complementary locking teeth 26, 27, and 28 are formed on the arms 17 and 18 for releasibly locking the clamp 15 around the tube 11 in each of the two closed positions. Preferably, the closed positions correspond to standard tube sizes. For example, the first closed position shown in FIG. 4 is used for retaining a tube having an outside diameter of 9.3 mm, while the second closed position shown in FIG. 5 retains a smaller tube have an outside diameter of 8.1 mm. Use of the proper closed position for the given tube size prevents sliding movement of the tube 11 within the clamp 15. In addition, the arms 17 and 18 preferably have attached inner liners 31 and 32 formed of rubber or other textured material which frictionally engages the tube 11 to further restrict sliding of the tube 11 within the clamp 15. To facilitate movement of the clamp 15 between the open and closed positions, a pair of grip extensions 34 and 35 are formed with the arm 17 and the mounting member 16, respectively, for being gripped by the thumb and forefinger of the user.

Operation of the Clamp 15

Figure 3:
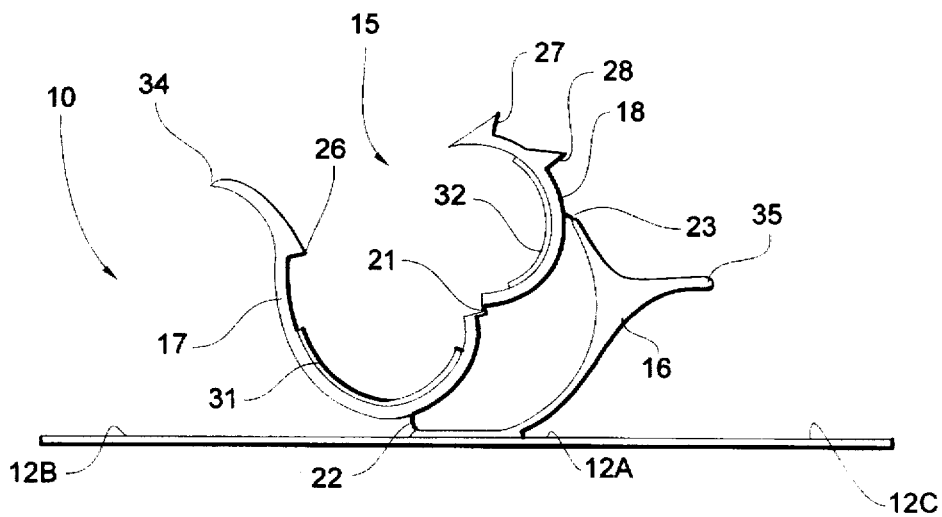
FIG. 3 is a top plan view of the tube-retaining device.

With the clamp 15 in the open position shown in FIG. 3, the tube 11 is placed between the arms 17 and 18 to engage the connecting point 21. Slight pressure applied at this point causes the arms 17 and 18 to snap closed. The arms 17 and 18 are then locked together around the tube 11 by squeezing the grip extensions 34 and 35 to mate the complementary teeth 26 and 27 or 28 in either of the first or second closed positions shown in FIGS. 4 and 5. The textured liners 31 and 32 further prevent sliding movement of the tube 11 within the clamp 15.

To release the tube 11 from the clamp 15, the user pulls outwardly on the extension 34 thereby separating the engaging teeth 26 and 27 or 28 and causing the arms 17 and 18 to snap open into the position shown in FIG. 3. The pivoting movement of the arms 17 and 18 at the hinged joints 22 and 23 and connecting point 21 acts to automatically eject the tube 11 from between the arms 17 and 18 for easy removal.

Figure 6:
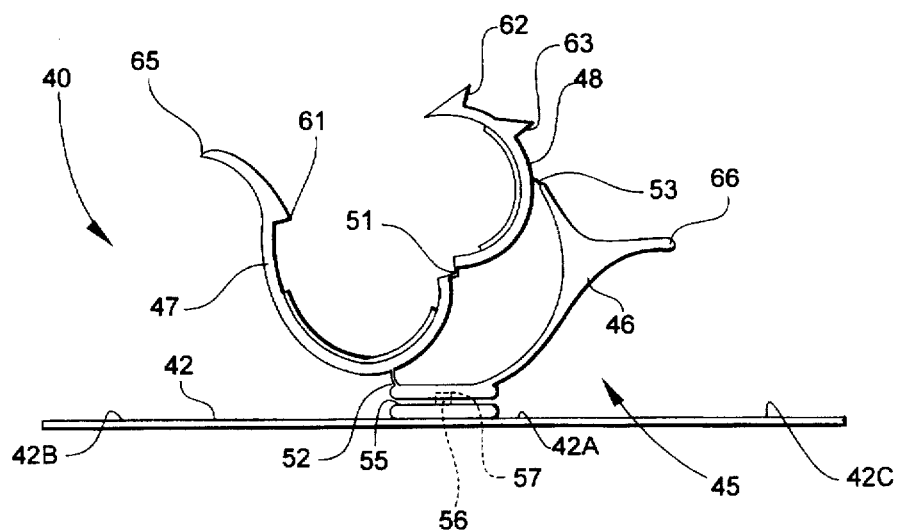
FIG. 6 is a side elevational view of a tube-retaining device according to a second preferred embodiment with the clamp in the open position.

A second embodiment of the invention is shown in FIG. 6. The tube-retaining device 40 includes a patch 42 formed of thin flexible plastic or paper and having an adhesive coating on its back surface for adhering the device 40 directly to the skin of the patient. The adhesive surface is covered with a release paper which is peeled away to expose the adhesive before positioning the patch 42 on the nose. The patch 42 has a front tab 42A which extends over the front of the nose and side tabs 42B and 42C extending outwardly on opposite sides of the nose, like that shown in FIGS. 1 and 2.

A clamp 45 is attached to the front tab 42A for holding the tube as it exits the nostril and extends upwardly over the nose of the patient. The clamp 45 is integrally formed of a molded plastic material, and includes a mounting member 46 and a pair of arcuate, slightly resilient arms 47 and 48. The arms 47 and 48 are pivotably connected together at a center connecting point 51, and are connected to the mounting member 46 at first and second hinged joints 52 and 53, respectively. The arms 47 and 48 are movable between an open tube-receiving position and one of two closed positions, as described above.

A mounting base 55 is attached to the patch 42, and includes a small protruding ball 56 which is received into a socket 57 formed in a bottom end of the mounting member 46 to interconnect the patch 42 and the clamp 45. The ball-and-socket attachment allows swivel movement of the clamp 45 to position the clamp opening on either side of the tube, as desired.

In addition, complementary locking teeth 61, 62, and 63 are formed on the arms 47 and 48 for releasibly locking the clamp 45 around the tube in each of the two closed positions. To facilitate movement of the clamp 45 between the open and closed positions, a pair of grip extensions 65 and 66 are formed with the arm 47 and the mounting member 46, respectively, for being gripped by the thumb and forefinger of the user.

Figure 7:
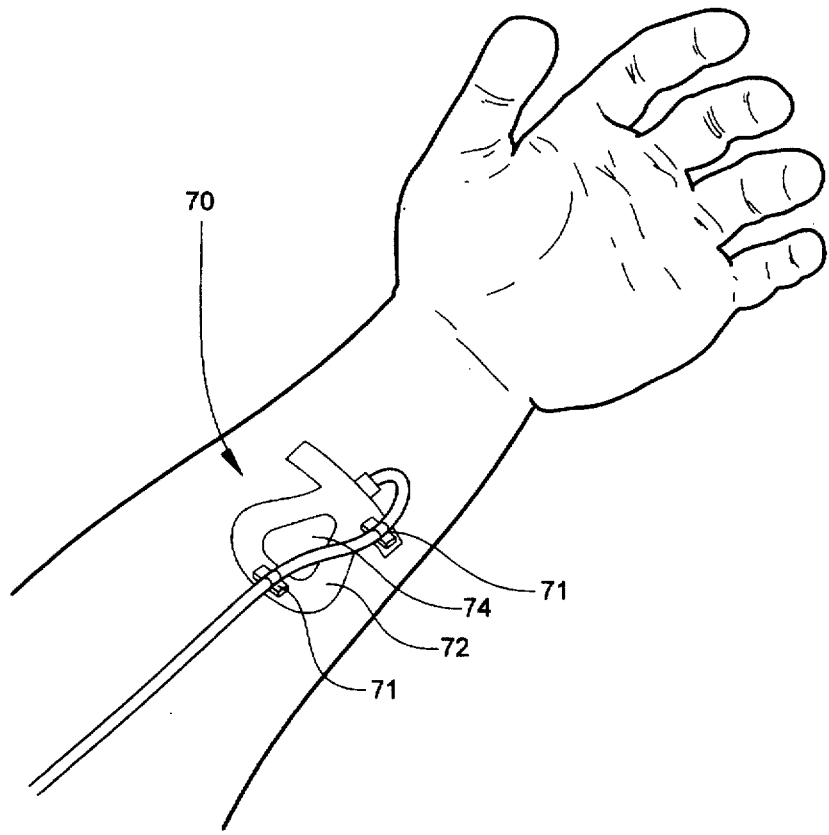
FIG. 7 is a perspective view of a tube-retaining device according to a further alternative embodiment of the invention, and showing the device secured to the forearm of a patient for securely retaining an IV catheter in a desired fixed position.

A still further embodiment of the tube-retaining device is shown in FIG. 7. This device 70 is especially applicable for retaining IV catheters, as shown, and may use one or more clamps 71. The clamp 71 is identical to either of the alternative embodiments described above. The patch 72 is a conventional patch having a generally transparent center window 74 to allow inspection of the tube insertion site.

A medical tube-retaining device is described above. Various details of the invention may be changed without departing from its scope. Furthermore, the foregoing description of the preferred embodiment of the invention and the best mode for practicing the invention are provided for the purpose of illustration only and not for the purpose of limitation—the invention being defined by the claims.

I claim:

1. In combination with a medical tube for being inserted into a patient's body at a tube insertion site, the improvement comprising a tube-retaining device for holding the tube in a fixed position on the patient proximate the insertion site, said tube-retaining device comprising:

(a) a base;
   (b) a mounting member carried by said base,
   (c) a clamp carried by said mounting member, and comprising first and second arcuate arms pivotably connected together at respective proximal ends;
   (d) first and second hinges interconnecting respective first and second arms and said mounting member for pivoting movement of said arms between an open tube-receiving position and a closed tube-enclosing position;
   (e) locking adjustment means for adjusting the space between said arms in the closed positions whereby said clamp is adjustable to accommodate different size tubes; and (f) first and second grip extensions formed on one of said first and second arms and on said mounting member, respectively, to facilitate locking adjustment of the space defined by said arms in the closed position.

2. A combination according to claim 1, wherein said base comprises a flexible patch with an adhesive coating on its back surface for adhering the tube-retaining device directly to the skin of the patient.

3. A combination according to claim 1, and comprising a release paper backing removably covering the back surface of said patch.

4. A combination according to claim 1, wherein the first and second arms of said clamp include a slip-resistant inner lining for frictionally engaging the tube.

5. A combination according to claim 4, wherein the slip-resistant inner lining is formed of rubber.

6. A combination according to claim 1, wherein said locking adjustment means comprises cooperating locking teeth formed on each of said first and second arms, and having respective engaging surfaces for providing locking adjustment of the space occupied by the tube and defined by said arms in the closed position.

7. A combination according to claim 1, and comprising swivel means for allowing swivel movement of said mounting member relative to said base.

8. A tube-retaining device for use with a medical tube for being inserted into a patient's body at a tube insertion site, the tube-retaining device being adapted for holding the tube in a fixed position on the patient proximate the insertion site, said tube-retaining device comprising:

(a) a base;

(b) a mounting member carried by said base;

(c) a clamp carried by said mounting member, and comprising first and second arcuate arms pivotably connected together at respective proximal ends;

(d) first and second hinges interconnecting respective first and second arms and said mounting member for pivoting movement of said arms between an open tube-receiving position and a closed tube-enclosing position;

(e) locking adjustment means for adjusting the space between said arms in the closed position, whereby said clamp is adjustable to accommodate different size tubes; and (f) first and second grip extensions formed on one of said first and second arms and on said mounting member, respectively, to facilitate locking adjustment of the space defined by said arms in the closed position.

9. A tube-retaining device according to claim 8, wherein said base comprises a flexible patch with an adhesive coating on its back surface for adhering the tube-retaining device directly to the skin of the patient.

10. A tube-retaining device according to claim 9, and comprising a release paper backing removably covering the back surface of said patch.

11. A tube-retaining device according to claim 8, wherein the arms of said clamp include a slip-resistant inner lining for frictionally engaging the tube.

12. A tube-retaining device according to claim 11, wherein the slip-resistant inner lining is formed of rubber.

13. A tube-retaining device according to claim 8, wherein said locking adjustment means comprises cooperating locking teeth formed on each of said first and second arms, and having respective engaging surfaces for providing locking adjustment of the space occupied by the tube and defined by said arms in the closed position.

14. A tube-retaining device according to claim 8, and comprising swivel means for allowing swivel movement of said mounting member relative to said base.

15. In combination with a medical tube for being inserted into a patient's body at a tube insertion site, the improvement comprising a tube-retaining device for holding the tube in a fixed position on the patient proximate the insertion site, said tube-retaining device comprising:

(a) a base;

(b) a mounting member carried by said base;

(c) a clamp carried by said mounting member, and comprising first and second arcuate arms pivotably connected together at respective proximal ends;

(d) first and second hinges interconnecting respective first and second arms and said mounting member for pivoting movement of said arms between an open tube-receiving position and a closed tube-enclosing position; and (e) first and second grip extensions formed on one of said first and second arms and on said mounting member, respectively, to facilitate movement of said arms between the open and closed positions.

16. A tube-retaining device for use with a medical tube for being inserted into a patient's body at a tube insertion site, the tube-retaining device being adapted for holding the tube in a fixed position on the patient proximate the insertion sire, said tube-retaining device comprising:

(a) a base;

(b) a mounting member carried by said base;

(c) a clamp carried by said mounting member, and comprising first and second arcuate arms pivotably connected together at respective proximal ends;

(d) first and second hinges interconnecting respective first and second arms and said mounting member for pivoting movement of said arms between an open tube-receiving position and a closed tube-enclosing position; and (e) first and second grip extensions formed on one of said first and second arms and on said mounting member, respectively, to facilitate movement of said arms between the open and closed positions.

* * * * *